United States Patent
Bohn et al.

(10) Patent No.: US 7,457,666 B2
(45) Date of Patent: Nov. 25, 2008

(54) RETROGRADE ATRIAL SENSING FOR IDENTIFYING SUB-THRESHOLD ATRIAL PACING

(75) Inventors: Derek D. Bohn, Woodbury, MN (US); Rajesh K. Gandhi, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 416 days.

(21) Appl. No.: 11/136,988

(22) Filed: May 25, 2005

(65) Prior Publication Data

US 2006/0271122 A1 Nov. 30, 2006

(51) Int. Cl.
*A61N 1/37* (2006.01)
*A61N 1/18* (2006.01)

(52) U.S. Cl. .......................................... 607/27; 607/28
(58) Field of Classification Search .............. 607/9, 607/14, 27, 28
See application file for complete search history.

(56) References Cited

U.S. PATENT DOCUMENTS

| | | | |
|---|---|---|---|
| 4,505,276 A * | 3/1985 | Markowitz et al. ........... 600/510 |
| 4,543,963 A * | 10/1985 | Gessman ..................... 600/515 |
| 4,569,350 A * | 2/1986 | Mumford et al. ............ 600/510 |
| 5,000,189 A | 3/1991 | Throne et al. |
| 5,217,021 A | 6/1993 | Steinhaus et al. |
| 5,350,410 A | 9/1994 | Kleks et al. |
| 5,374,280 A | 12/1994 | den Dulk |
| 5,447,519 A | 9/1995 | Peterson |
| 5,458,623 A | 10/1995 | Lu et al. |
| 5,601,615 A | 2/1997 | Markowitz et al. |
| 5,653,738 A | 8/1997 | Sholder et al. |
| 5,683,431 A | 11/1997 | Wang |
| 5,713,933 A | 2/1998 | Greeninger |
| 5,766,229 A | 6/1998 | Bornzin |
| 5,779,645 A | 7/1998 | Olson et al. |
| 5,817,027 A | 10/1998 | Arand et al. |
| 5,843,137 A | 12/1998 | Condie et al. |
| 5,857,977 A | 1/1999 | Caswell et al. |
| 5,871,509 A | 2/1999 | Noren |
| 6,038,474 A | 3/2000 | Zhu et al. |

(Continued)

FOREIGN PATENT DOCUMENTS

EP 1 116 494 A 7/2001

(Continued)

*Primary Examiner*—Carl H. Layno
*Assistant Examiner*—Tammie K. Heller
(74) *Attorney, Agent, or Firm*—Hollingsworth & Funk, LLC

(57) ABSTRACT

Methods and systems for delivering a pacing pulse to an atrium during a cardiac cycle. A retrograde P-wave may be identified during the cardiac cycle, indicative of sub-threshold atrial pacing. Delivery of the pacing pulse to the atrium may be adjusted in a subsequent cardiac cycle in response to identifying the retrograde P-wave. Adjusting delivery of the pacing pulse may involve initiating an atrial capture threshold test, temporarily increasing one or both of the pacing pulse amplitude and pulse width, and/or re-evaluating one or both of the pacing pulse amplitude and pulse width. Adjusting delivery of the pacing pulse may also involve altering the timing of a scheduled atrial capture threshold test. During an atrial capture threshold test, a retrograde P-wave template may be generated in response to atrial non-capture sensed during the atrial capture threshold test, and used to identify subsequent retrograde P-waves.

17 Claims, 5 Drawing Sheets

U.S. PATENT DOCUMENTS

| | | | |
|---|---|---|---|
| 6,052,620 | A | 4/2000 | Gillberg et al. |
| 6,076,014 | A | 6/2000 | Alt |
| 6,101,416 | A | 8/2000 | Sloman |
| 6,128,535 | A | 10/2000 | Maarse |
| 6,163,724 | A | 12/2000 | Hemming et al. |
| 6,175,766 | B1 | 1/2001 | Bornzin et al. |
| 6,221,011 | B1 | 4/2001 | Bardy |
| 6,259,950 | B1 * | 7/2001 | Mann et al. .............. 607/28 |
| 6,270,457 | B1 | 8/2001 | Bardy |
| 6,275,731 | B1 | 8/2001 | Zhu et al. |
| 6,277,072 | B1 | 8/2001 | Bardy |
| 6,280,380 | B1 | 8/2001 | Bardy |
| 6,312,378 | B1 | 11/2001 | Bardy |
| 6,336,903 | B1 | 1/2002 | Bardy |
| 6,358,203 | B2 | 3/2002 | Bardy |
| 6,363,281 | B1 | 3/2002 | Zhu et al. |
| 6,368,284 | B1 | 4/2002 | Bardy |
| 6,389,316 | B1 * | 5/2002 | Bornzin et al. ............ 607/28 |
| 6,398,728 | B1 | 6/2002 | Bardy |
| 6,408,210 | B1 | 6/2002 | Bornzin et al. |
| 6,418,343 | B1 | 7/2002 | Zhang et al. |
| 6,440,066 | B1 | 8/2002 | Bardy |
| 6,449,503 | B1 | 9/2002 | Hsu |
| 6,456,881 | B1 | 9/2002 | Bornzin et al. |
| 6,473,649 | B1 | 10/2002 | Gryzwa et al. |
| 6,498,949 | B2 | 12/2002 | Levine et al. |
| 6,505,071 | B1 | 1/2003 | Zhu et al. |
| 6,611,714 | B1 | 8/2003 | Mo |
| 6,684,100 | B1 | 1/2004 | Sweeney et al. |
| 6,697,673 | B1 | 2/2004 | Lu |
| 6,721,601 | B1 | 4/2004 | Bornzin et al. |
| 6,925,326 | B1 | 8/2005 | Levine et al. |
| 6,950,704 | B1 | 9/2005 | Bradley |
| 7,123,954 | B2 | 10/2006 | Narayan et al. |
| 7,177,685 | B2 | 2/2007 | Lincoln et al. |
| 2002/0120303 | A1 | 8/2002 | Levine et al. |
| 2003/0125777 | A1 | 7/2003 | Ding et al. |
| 2004/0260348 | A1 | 12/2004 | Bakken et al. |
| 2005/0080347 | A1 | 4/2005 | Sheth et al. |
| 2005/0131476 | A1 | 6/2005 | Kim et al. |
| 2005/0131477 | A1 | 6/2005 | Meyer et al. |
| 2006/0129197 | A1 | 6/2006 | Zhang et al. |
| 2006/0129198 | A1 | 6/2006 | Zhang et al. |

FOREIGN PATENT DOCUMENTS

| | | |
|---|---|---|
| EP | 1116494 | 7/2001 |
| WO | WO 2006/065707 | 6/2006 |

* cited by examiner

RETROGRADE ATRIAL SENSING FOR IDENTIFYING SUB-THRESHOLD ATRIAL PACING

FIELD OF THE INVENTION

The present invention relates generally to implantable medical devices and, more particularly, to cardiac systems and methods that use retrograde atrial sensing to identify atrial loss of capture.

BACKGROUND OF THE INVENTION

When functioning normally, the heart produces rhythmic contractions and is capable of efficiently pumping blood throughout the body. However, due to disease or injury, the heart rhythm may become irregular resulting in diminished pumping efficiency.

Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically include circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal following the contraction is denoted the captured response (CR). The captured response may include an electrical signal, denoted the evoked response signal, associated with the heart contraction, along with a superimposed signal associated with residual post pace polarization at the electrode-tissue interface.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold may be required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Retrograde conduction may occur, for example, when a depolarization wave initiated in a ventricle by a pacing pulse or intrinsic activation travels back to the atrium producing a retrograde P-wave. Retrograde P-waves may inhibit effective atrial pacing. A pacing pulse delivered to the atrium will not result in capture if the atrial tissue is refractory due to a retrograde P-wave. Further, retrograde conduction to the atrium may cause pacemaker mediated tachycardia.

There is a need in the technology for methods and systems that reliably determine if a pacing pulse captures an atrium. There is a further need for methods and systems that provide atrial retrograde management. The present invention fulfills these and other needs.

SUMMARY OF THE INVENTION

The present invention is directed to methods and systems for detecting sub-threshold atrial pacing. Embodiments of the invention involve delivering a pacing pulse to an atrium during a cardiac cycle. A retrograde P-wave may be identified during the cardiac cycle, the retrograde P-wave indicative of sub-threshold atrial pacing. Delivery of the pacing pulse to the atrium may be adjusted in a subsequent cardiac cycle in response to identifying the retrograde P-wave.

For example, adjusting delivery of the pacing pulse may involve initiating an atrial capture threshold test, temporarily increasing one or both of the pacing pulse amplitude and pulse width, and/or re-evaluating one or both of the pacing pulse amplitude and pulse width. Adjusting delivery of the pacing pulse may also involve altering the timing of a scheduled atrial capture threshold test. During an atrial capture threshold test, a retrograde P-wave template may be generated in response to atrial non-capture sensed during the atrial capture threshold test, and used to identify subsequent retrograde P-waves.

Identifying retrograde P-waves may involve determining one or more of the frequency content, amplitude, slew rate, and timing of a cardiac response to the pacing pulse. The presence of the retrograde P-wave may be confirmed prior to adjusting delivery of the pacing pulse. The retrograde P-wave may be during a post ventricular atrial refractory period, such as within a range of about 200 milliseconds and about 300 milliseconds after a ventricular pace.

Further embodiments of the present invention are directed to cardiac systems having implantable electrodes configured for one or more of sensing a cardiac signal and delivering cardiac pacing pulses to a patient. A housing may be configured for implantation in the patient, and house a controller. The controller may be coupled to the implantable electrodes, and configured to deliver a pacing pulse to an atrium of the patient's heart during a cardiac cycle, identify a retrograde P-wave indicative of sub-threshold atrial pacing during the cardiac cycle, and adjust delivery of the pacing pulse to the atrium in a subsequent cardiac cycle in response to identifying the retrograde P-wave. The controller may be configured to perform an atrial capture threshold test, generate a retrograde P-wave template in response to atrial non-capture sensed during the atrial capture threshold test, and use the generated retrograde P-wave template to identify the retrograde P-wave.

The above summary of the present invention is not intended to describe each embodiment or every implementation of the present invention. Advantages and attainments, together with a more complete understanding of the invention, will become apparent and appreciated by referring to the following detailed description and claims in conjunction with the accompanying drawings.

Figure 1A:
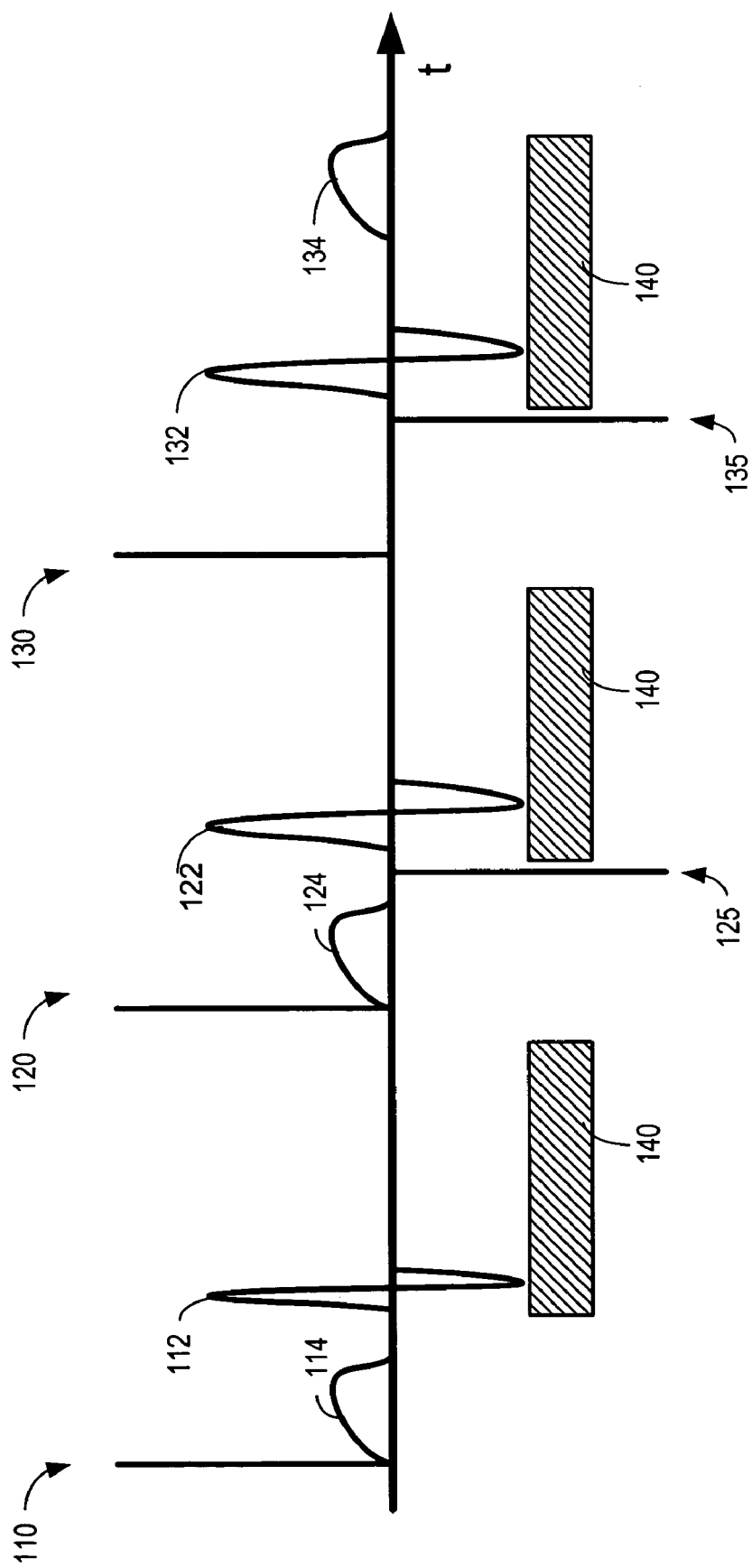
FIG. 1A is a graph illustrating atrial loss of capture in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown, by way of illustration, various embodiments by which the invention may be practiced. It is to be understood that other embodiments may be utilized, and structural and functional changes may be made without departing from the scope of the present invention.

After delivery of a pacing pulse to a heart chamber, various cardiac responses to the pacing pulse are possible. In one scenario, the pacing pulse may generate a propagating wavefront of depolarization resulting in a contraction of the heart chamber. In this scenario, the pacing pulse is said to have captured the heart chamber. Capture of the heart chamber may occur if the pacing pulse has sufficient energy and is delivered during a non-refractory period. If the pacing pulse does not produce contraction of the chamber, the cardiac response is referred to as non-capture or loss of capture. Non-capture may occur, for example, if the pacing pulse energy is too low, and/or if the pacing pulse is delivered during a refractory period of the cardiac tissue.

Methods in accordance with the present invention may be used to sense retrograde atrial conduction and identify sub-threshold atrial pacing. The minimum pacing energy that produces capture is referred to as the capture threshold. It is desirable for a pace pulse to have sufficient energy to capture the heart without expending excess energy above the capture threshold.

Those skilled in the art will appreciate that reference to a capture threshold testing procedure indicates a method of determining the capture threshold in one or more of the left atrium, right atrium, left ventricle, and right ventricle. In such a procedure, the pacemaker, automatically or upon command, initiates a search for the capture threshold of the selected heart chamber. The capture threshold is defined as the lowest pacing energy that consistently captures the heart.

In one example of a capture threshold test, the pacemaker delivers a sequence of pacing pulses to the heart and detects the cardiac responses to the pace pulses. The energy of the pacing pulses may be decreased in discrete steps until a predetermined number of loss-of-capture responses occur. The pacemaker may increase the stimulation energy in discrete steps until a predetermined number of capture responses occur to confirm the capture threshold. A capture threshold test may be performed using cardiac response classification methods in accordance with the present invention.

Other procedures for implementing capture threshold testing may be utilized. In one example, the pacing energy may be increased in discrete steps until capture is detected. In another example, the pacing energy may be adjusted according to a binomial search pattern.

Embodiments of the invention are directed to methods and systems for determining if an atrial pacing pulse captures or fails to capture the atrium. Loss of capture determination may be based on detection of a ventricular depolarization wave that travels back to the atrium, designated retrograde conduction. This retrograde depolarization wave may be sensed and used to detect sub-threshold atrial pacing in accordance with the present invention.

When a ventricular depolarization occurs, either intrinsically, or as a result of a ventricular pace, the depolarization wavefront may travel towards the atrium if the atrial tissue is not in its refractory period. If the myocardial tissue of the atrium is not refractory (i.e., if there was no intrinsic P-wave or the atrium was not captured by an atrial pacing pulse preceding the ventricular depolarization), then the wavefront initiated by the ventricular depolarization is more likely to be retrogradely conducted and sensed in the atrium as a retrograde P-wave. Thus, sensing a retrograde P-wave indicates that the atrial pacing pulse did not capture the atrium.

Auto-threshold algorithms run tests periodically to determine the pacing threshold, but may not verify capture on a beat-by-beat basis. Large pacing margins are used to ensure pacing pulses capture the heart during the time between tests. One weakness of these algorithms is made evident if thresholds rise enough between subsequent tests that pacing stimulus fails to capture the chamber. If this is not accounted for, extended periods of sub-threshold pacing may occur.

If the atrial threshold rises above the pacing voltage and the atrial paces do not capture the atrium, the following ventricular pace (or sense) can retrograde back to the atrium and appear as an atrial sense. These retrograde senses may cause pacemaker mediated tachycardia events.

For patients with intact atrio-ventricular conduction, retrograde signals may be used in accordance with the present invention as an indicator that the device is atrial pacing sub-threshold. Detection of these retrograde events may be used as a signal to run new atrial threshold testing or to increase atrial pacing amplitude, for example. Detection of retrograde conduction may be used to trigger a validation algorithm that validates sub-threshold pacing is occurring before performing mitigation, to improve robustness of the system.

Implantable cardiac devices in accordance with embodiments of the present invention may react to the detection of sub-threshold pacing in several ways. Existing hardware may include peak detection circuitry that may be used to sense retrograde conduction based on the timing of the detected peak of a p-wave. This may trigger a test out of a normal sequence, such as if tests are scheduled to regularly occur. Retrograde conduction detection may cause a threshold test to be initiated any time it is detected, or detection of retrograde conduction may initiate a temporary increase of the pacing amplitude, pulse width, or both amplitude and pulse width until the next scheduled threshold test occurs.

Retrograde atrial sensing outside of the ventricular refractory period may result in pacemaker mediated tachycardia if it is not mitigated. Initiating a threshold test and/or temporarily raising pacing amplitude and/or pulse width may mitigate the pacemaker mediated tachycardia, for example.

If an implantable cardiac device includes signal processing capability within the pulse generator, such as a digital signal processor (DSP), the DSP may be used to detect the retrograde conduction. The DSP may identify retrograde conduction using one or more of frequency content, amplitude, slew rate, timing, or a combination of these parameters when analyzing the cardiac response to pacing. Further, a DSP may be trained to recognize retrograde conduction. For example, during a standard threshold test pacing is intentionally performed both above threshold and below threshold. The response to below threshold pacing may be used to train the DSP to recognize retrograde conduction in an individual patient. The DSP may create one or more templates of retrograde conduction, using information determined during threshold tests.

Implantable cardiac devices that incorporate retrograde conduction detection may utilize reduced pacing margins to conserve energy. Retrograde conduction detection may then be used to mitigate the effects from changing thresholds between threshold tests, allowing smaller margins above threshold to be used. Further, implantable cardiac devices may eliminate the regular scheduling of threshold tests, and use retrograde conduction detection to initiate threshold testing only when it is needed.

FIG. 1A is a graph illustrating a method of using retrograde conduction to identify sub-threshold pacing in accordance with embodiments of the invention. This method may be used, for example, in a dual chamber device. When atrial capture is lost, AV synchrony may be disrupted, and a ventricular pulse may occur after the failed atrial pulse when an atrioventricular delay expires. Because the ventricle is activated before the atrium, the excitation may travel up to activate the atrium as retrograde conduction.

In the graph of FIG. 1A, an atrial pacing pulse 110 that captures the atrium is followed by a p-wave 114, and an intrinsic ventricular response 112, which is a QRS complex. A post ventricular atrial refractory period (PVARP) 140 is illustrated following the intrinsic ventricular response 112. This is an atrial paced heartbeat with intrinsic ventricular response.

The next heartbeat begins with an atrial pacing pulse 120 that captured the atrium. The atrial pacing pulse 120 is followed by an atrial evoked response 124. A ventricular pacing pulse 125 is delivered which captures the ventricle producing a paced QRS complex 122. The paced QRS complex 122 shows a widened QRS complex relative to the intrinsic ventricular response 112. A PVARP 140 is illustrated following the ventricular pacing pulse 125.

The final heartbeat of FIG. 1A illustrates an atrial retrograde conduction. The atrial pacing pulse 130 does not capture the atrium, thus an atrial evoked response is not sensed. The atrial pacing pulse 130 is followed, after an atrioventricular delay, by a ventricular pacing pulse 135, and a paced QRS complex 132, showing a widened QRS complex relative to the intrinsic ventricular response 112. A PVARP 140 is illustrated following the ventricular pulse 135. An atrial P-wave 134 is illustrated within the PVARP 140 following the ventricular pulse 135. The retrograde P-wave is produced by a depolarization wavefront initiated by the ventricular pulse 135 and conducted to the atrium. If retrograde conduction occurs in close proximity to a scheduled atrial pacing pulse, capture of the atrium may not occur regardless of the pulse being greater than a capture threshold.

Figure 1B:
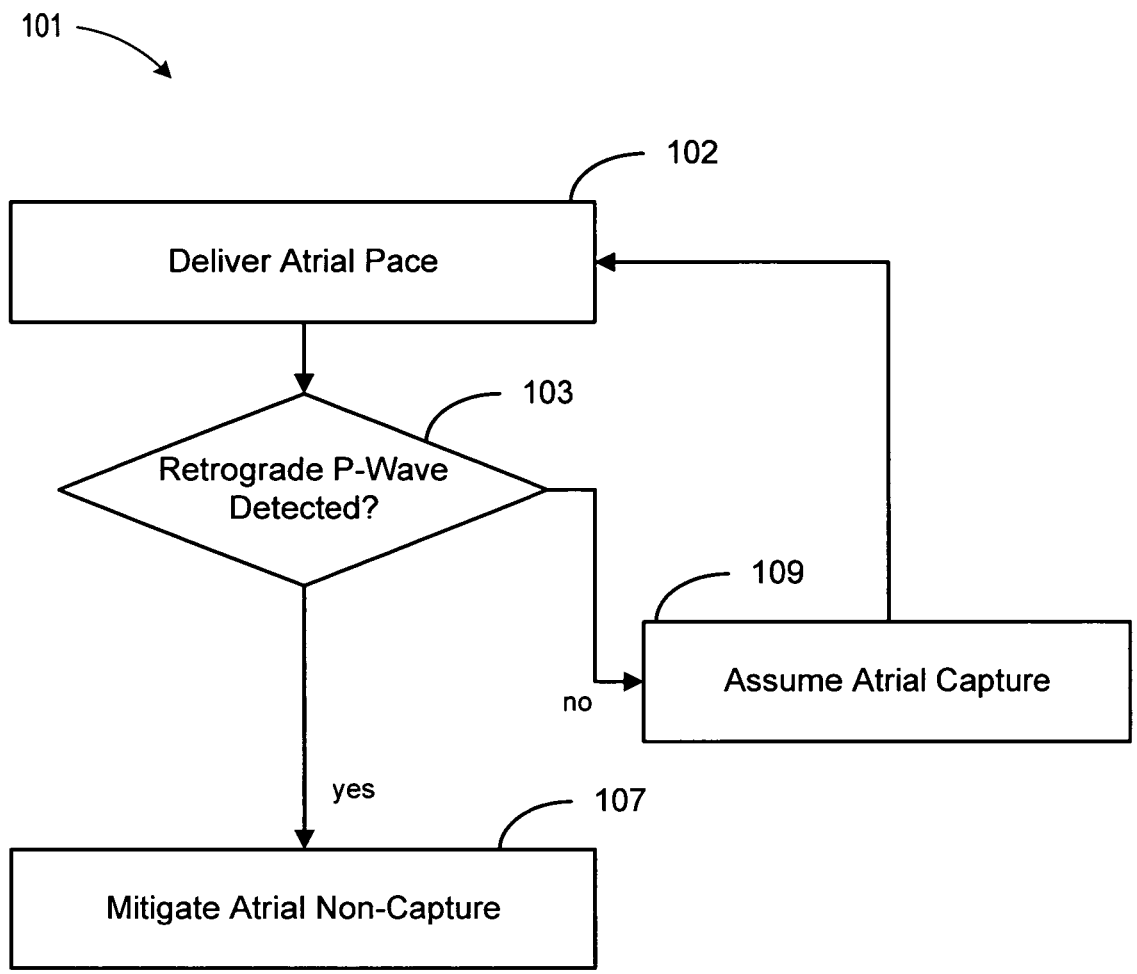
FIG. 1B is a flowchart illustrating a method of detecting sub-threshold atrial pacing in accordance with embodiments of the invention.
Figure 1C:
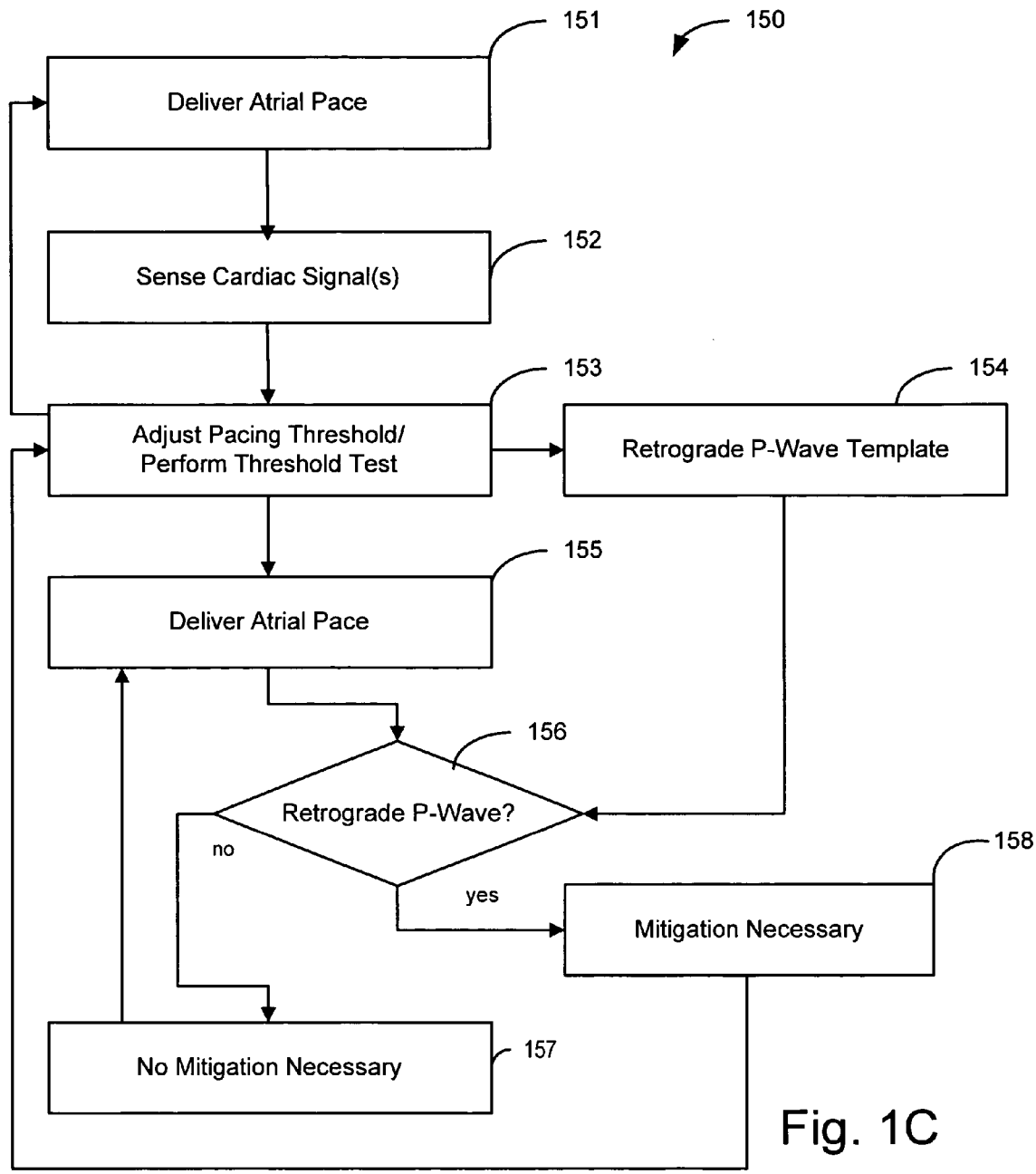
FIG. 1C is a flowchart illustrating a method of detecting sub-threshold atrial pacing in accordance with other embodiments of the invention.

FIGS. 1B and 1C are flowcharts illustrating detection of sub-threshold atrial pacing in accordance with embodiments of the invention. The flowchart of FIG. 1B illustrates a method 101 of atrial non-capture detection based on a sensed retrograde P-wave. A pacing pulse is delivered 102 to an atrium during a cardiac cycle. The system identifies 103 if a retrograde P-wave is responsive to intrinsic ventricular activation or a ventricular pace.

If the retrograde P-wave is identified 103, then atrial non-capture is determined, and mitigation 107 may be performed, such as by temporarily increasing amplitude and/or pulse width, initiating a threshold test, or other action as described above. If the retrograde P-wave is not identified 103, then the system may classify 109 the cardiac response to the atrial pace as a captured response.

The flowchart of FIG. 1C illustrates a method 150 of detecting sub-threshold pacing in accordance with embodiments of the present invention. Atrial paces are delivered 151 to a patient's heart as part of a threshold detection test 153. Cardiac signals are sensed 152 responsive to the paces 151. The capture threshold test 153 is performed for pacing levels both above and below the capture threshold, and a template 154 is created. The template 154 corresponds to retrograde conduction.

Subsequent pacing 155 is delivered, and the system identifies 156 if a retrograde P-wave occurs using the template 154. If the retrograde P-wave is identified 156, then atrial non-capture is determined, and mitigation 158 may be performed, such as by temporarily increasing amplitude and/or pulse width, initiating another threshold test 153, or other action as described above. If the retrograde P-wave is not identified 156, then no mitigation 157 is needed, and the system continues to pace 155 at its current settings.

The embodiments of the present system illustrated herein are generally described as being implemented in an implantable cardiac pacemaker/defibrillator (PD) that may operate in numerous pacing modes known in the art. Various types of single and multiple chamber implantable cardiac defibrillators are known in the art and may be used in connection with detection of atrial non-capture in accordance with the present invention. The methods of the present invention may also be implemented in a variety of implantable or patient-external cardiac rhythm management devices, including dual chamber pacemakers, defibrillators, cardioverters, bi-ventricular pacemakers, cardiac resynchronizers, for example.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

Figure 2:
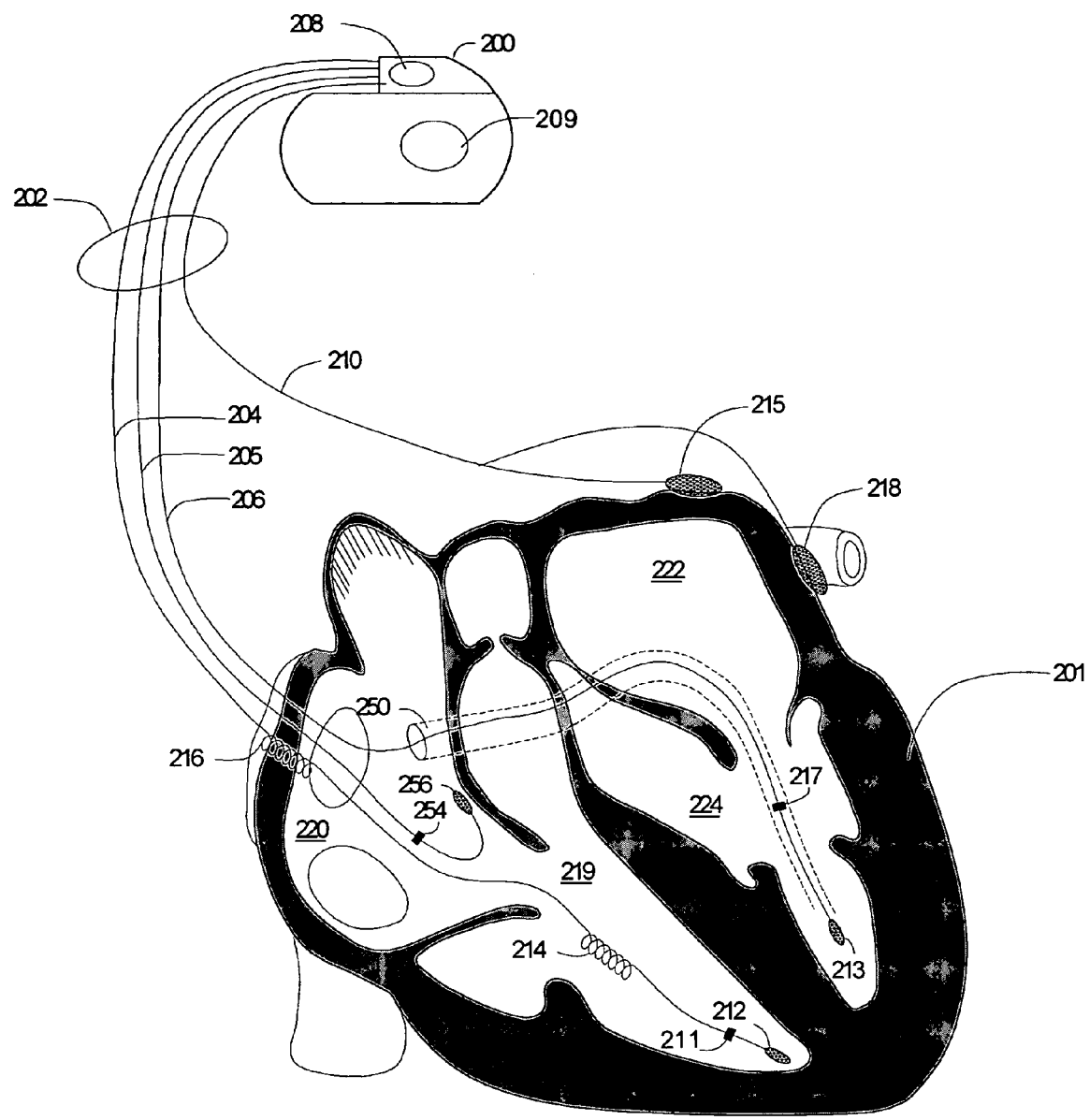
FIG. 2 illustrates an implantable cardiac rhythm management system that may be used in connection with detection of sub-threshold atrial pacing methodologies in accordance with embodiments of the invention.

Referring now to FIG. 2 of the drawings, there is shown a cardiac rhythm management system that may be used to implement detection of atrial non-capture in accordance with the present invention. The cardiac rhythm management (CRM) system in FIG. 2 includes a PD 200 electrically and physically coupled to a lead system 202. The housing and/or header of the PD 200 may incorporate one or more electrodes 208, 209 used to provide electrical stimulation energy to the heart and to sense cardiac electrical activity. The PD 200 may utilize all or a portion of the PD housing as a can electrode 209. The PD 200 may include an indifferent electrode 208 positioned, for example, on the header or the housing of the PD 200. If the PD 200 includes both a can electrode 209 and an indifferent electrode 208, the electrodes 208, 209 typically are electrically isolated from each other.

The lead system 202 is used to detect electric cardiac signals produced by the heart 201 and to provide electrical energy to the heart 201 under certain predetermined conditions to treat cardiac arrhythmias. The lead system 202 may include one or more electrodes used for pacing, sensing, and/or defibrillation. In the embodiment shown in FIG. 2, the lead system 202 includes an intracardiac right ventricular (RV) lead system 204, an intracardiac right atrial (RA) lead system 205, an intracardiac left ventricular (LV) lead system 206, and an extracardiac left atrial (LA) lead system 210. The lead system 202 of FIG. 2 illustrates one embodiment that may be used in connection with the methodologies described herein. Other leads and/or electrodes may additionally or alternatively be used.

The lead system 202 may include intracardiac leads 204, 205, 206 implanted in a human body with portions of the intracardiac leads 204, 205, 206 inserted into a heart 290. The intracardiac leads 204, 205, 206 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 2, the lead system 202 may include one or more extracardiac leads 210 having electrodes, e.g., epicardial electrodes, positioned at locations outside the heart for sensing and/or pacing one or more heart chambers.

The right ventricular lead system 204 illustrated in FIG. 2 includes an SVC-coil 216, an RV-coil 214, an RV-ring electrode 211, and an RV-tip electrode 212. The right ventricular lead system 204 extends through the right atrium 220 and into the right ventricle 219. In particular, the RV-tip electrode 212, RV-ring electrode 211, and RV-coil electrode 214 are positioned at appropriate locations within the right ventricle for sensing and delivering electrical stimulation pulses to the heart. The SVC-coil 216 is positioned at an appropriate location within the right atrium chamber of the heart 290 or a major vein leading to the right atrial chamber of the heart 290.

In one configuration, the RV-tip electrode 212 referenced to the can electrode 209 may be used to implement unipolar pacing and/or sensing in the right ventricle. Bipolar pacing and/or sensing in the right ventricle may be implemented using the RV-tip 212 and RV-ring 211 electrodes. In yet another configuration, the RV-ring 211 electrode may optionally be omitted, and bipolar pacing and/or sensing may be accomplished using the RV-tip electrode 212 and the RV-coil 214, for example. The right ventricular lead system 204 may be configured as an integrated bipolar pace/shock lead. The RV-coil 214 and the SVC-coil 216 are defibrillation electrodes.

The left ventricular lead 206 includes an LV distal electrode 213 and an LV proximal electrode 217 located at appropriate locations in or about the left ventricle for pacing and/or sensing the left ventricle. The left ventricular lead 206 may be guided into the right atrium of the heart via the superior vena cava. From the right atrium, the left ventricular lead 206 may be deployed into the coronary sinus ostium, the opening of the coronary sinus. The lead 206 may be guided through the coronary sinus to a coronary vein of the left ventricle. This vein is used as an access pathway for leads to reach the surfaces of the left ventricle that are not directly accessible from the right side of the heart. Lead placement for the left ventricular lead 206 may be achieved via subclavian vein access and a preformed guiding catheter for insertion of the LV electrodes 213, 217 adjacent to the left ventricle.

Unipolar pacing and/or sensing in the left ventricle may be implemented, for example, using the LV distal electrode 213 referenced to the can electrode 209. The LV distal electrode 213 and the LV proximal electrode 217 may be used together as bipolar sense and/or pace electrodes for the left ventricle. The left ventricular lead 206 and the right ventricular lead 204, in conjunction with the PD 200, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 205 includes a RA-tip electrode 256 and an RA-ring electrode 254 positioned at appropriate locations in the right atrium for sensing and pacing the right atrium. In one configuration, the RA-tip 256 referenced to the can electrode 209, for example, may be used to provide unipolar pacing and/or sensing in the right atrium 220. In another configuration, the RA-tip electrode 256 and the RA-ring electrode 254 may be used to effect bipolar pacing and/or sensing.

Detection of a right ventricular signal conducted to the atria may be detected by the atrial electrode(s) such as the RA-tip electrode 256 and/or the RA-ring electrode 254, or using other leads such as the LV distal electrode 213 and/or the LV proximal electrode 217. Similarly, detection of a left ventricular retrograde signal to the atria may be detected by the right ventricular lead system 204 or other leads.

FIG. 2 illustrates one embodiment of a left atrial lead system 210. In this example, the left atrial lead 210 is implemented as an extracardiac lead with an LA distal electrode 218 and LA proximal electrode 215 positioned at appropriate locations outside the heart 201 for sensing and pacing the left atrium. Unipolar pacing and/or sensing of the left atrium may be accomplished, for example, using the LA distal electrode 218 to the can 209 pacing vector. Bipolar pacing and/or sensing of the left atrium may be accomplished through the use of the LA distal electrode 218 and the LA proximal electrode 215.

Figure 3:
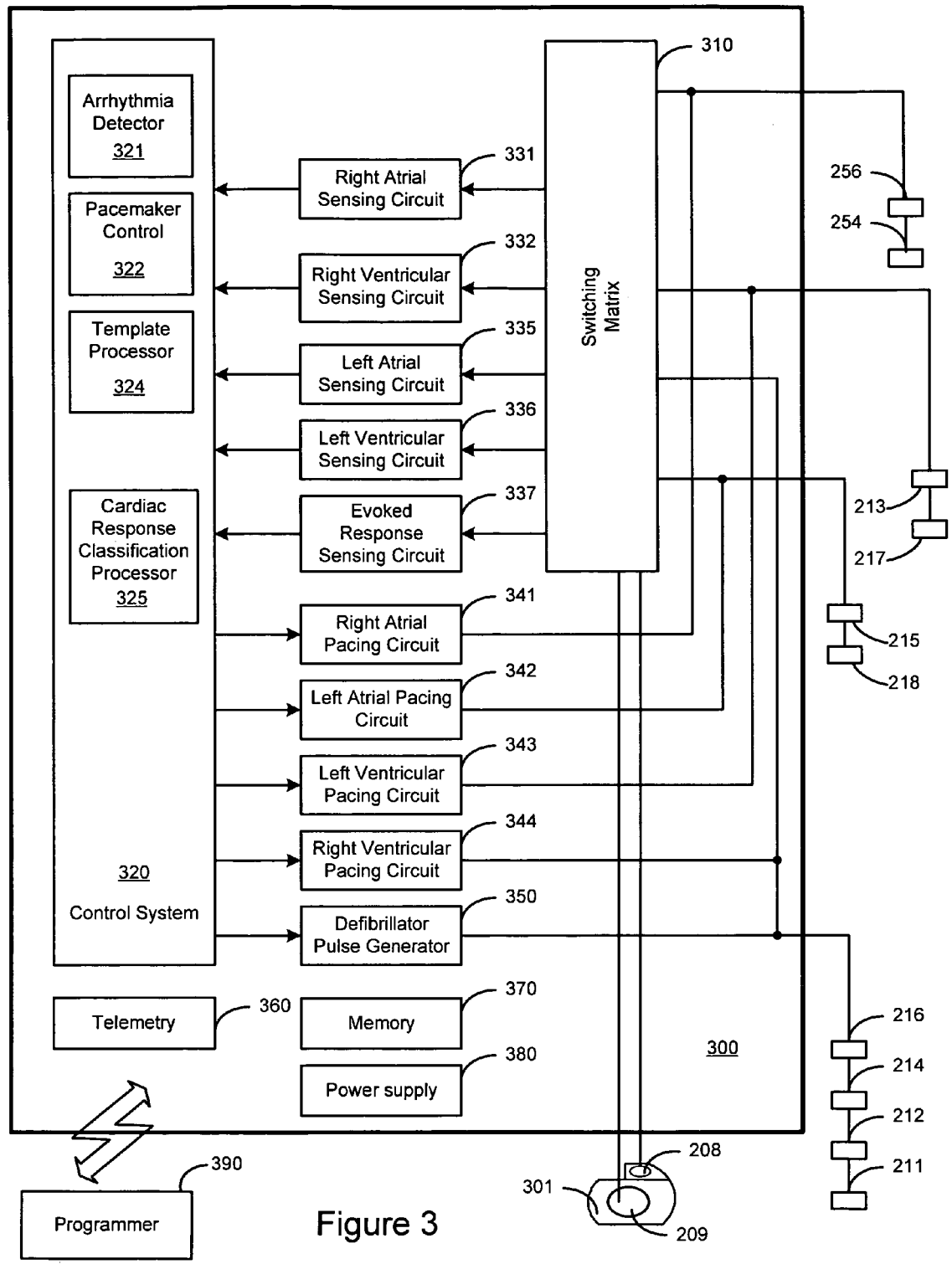
FIG. 3 is a block diagram of an implantable medical device that may be used to detect sub-threshold atrial pacing and manage atrial retrograde conduction in accordance with embodiments of the invention.

Referring now to FIG. 3, there is shown an embodiment of a cardiac pacemaker/defibrillator 300 suitable for implementing detection of atrial non-capture in accordance with the present invention. FIG. 3 shows a cardiac pacemaker/defibrillator divided into functional blocks. It is understood by those skilled in the art that there exist many possible configurations in which these functional blocks can be arranged. The example depicted in FIG. 3 is one possible functional arrangement. Other arrangements are also possible. For example, more, fewer or different functional blocks may be used to describe a cardiac pacemaker/defibrillator suitable for implementing the methodologies of the present invention. In addition, although the cardiac pacemaker/defibrillator 300 depicted in FIG. 3 contemplates the use of a programmable microprocessor-based logic circuit, other circuit implementations may be utilized.

The cardiac pacemaker/defibrillator 300 depicted in FIG. 3 includes circuitry for receiving cardiac signals from a heart and delivering electrical stimulation energy to the heart in the form of pacing pulses or defibrillation shocks. In one embodiment, the circuitry of the cardiac pacemaker/defibrillator 300 is encased and hermetically sealed in a housing 301 suitable for implanting in a human body. Power to the cardiac pacemaker/defibrillator 300 is supplied by an electrochemical battery 380. A connector block (not shown) is attached to the housing 301 of the cardiac pacemaker/defibrillator 300 to allow for the physical and electrical attachment of the lead system conductors to the circuitry of the cardiac pacemaker/defibrillator 300.

The cardiac pacemaker/defibrillator 300 may be a programmable microprocessor-based system, including a control system 320 and a memory 370. The memory 370 may store parameters for various pacing, defibrillation, and sensing modes, along with other parameters. Further, the memory 370 may store data indicative of cardiac signals received by other components of the cardiac pacemaker/defibrillator 300. The memory 370 may be used, for example, for storing historical EGM and therapy data. The historical data storage may include, for example, data obtained from long-term patient monitoring used for trending or other diagnostic purposes. Historical data, as well as other information, may be transmitted to an external programmer unit 390 as needed or desired.

The control system 320 may cooperate with other components of the cardiac pacemaker/defibrillator 300 to control the operations of the cardiac pacemaker/defibrillator 300. In one example, the cardiac pacemaker/defibrillator 300 may incorporate a sensor for determining the patient's hemodynamic need. The sensor output may be utilized by the control system 320 to deliver pacing at a rate adapted to the activity level of the patient. In some implementations, the cardiac pacemaker/defibrillator 300 may include components of an accelerometer and/or a transthoracic impedance sensor for determining the activity level and/or respiration rate of the patient.

The control system 320 depicted in FIG. 3 incorporates a cardiac response classification processor 325 for determining cardiac responses to pacing stimulation in accordance with various embodiments of the present invention. The control system 320 may include additional functional components including a pacemaker control circuit 322, an arrhythmia detector 321, and a template processor 324, along with other components for controlling the operations of the cardiac pacemaker/defibrillator 300.

Telemetry circuitry 360 may be implemented to provide communications between the cardiac pacemaker/defibrillator 300 and an external programmer unit 390. In one embodiment, the telemetry circuitry 360 and the programmer unit 390 communicate using a wire loop antenna and a radio frequency telemetric link, as is known in the art, to receive and transmit signals and data between the programmer unit 390 and the telemetry circuitry 360. In this manner, programming commands and other information may be transferred to the control system 320 of the cardiac pacemaker/defibrillator 300 from the programmer unit 390 during and after implant. In addition, stored cardiac data pertaining to capture threshold, capture detection and/or cardiac response classification, for example, along with other data, may be transferred to the programmer unit 290 from the cardiac pacemaker/defibrillator 300.

In the embodiment of the cardiac pacemaker/defibrillator 300 illustrated in FIG. 3, electrodes RA-tip 256, RA-ring 254, RV-tip 212, RV-ring 211, RV-coil 214, SVC-coil 216, LV distal electrode 213, LV proximal electrode 217, LA distal electrode 218, indifferent electrode 208, and can electrode 209 are coupled through a switch matrix 310 to sensing circuits 331-337.

A right atrial sensing circuit 331 serves to detect and amplify electrical signals from the right atrium of the heart. Unipolar sensing may be implemented, for example, by sensing voltages developed between the RA-tip 256 and the can electrode 209. Outputs from the right atrial sensing circuit are coupled to the control system 320.

A right ventricular sensing circuit 332 serves to detect and amplify electrical signals from the right ventricle of the heart. Right ventricular cardiac signals sensed through use of the RV-tip 212 electrode are right ventricular near-field signals and are denoted RV rate channel signals. A bipolar RV rate channel signal may be sensed as a voltage developed between the RV-tip 212 and the RV-ring 211. Alternatively, bipolar sensing in the right ventricle may be implemented using the RV-tip electrode 212 and the RV-coil 214. Unipolar rate channel sensing in the right ventricle may be implemented, for example, by sensing voltages developed between the RV-tip 212 and the can electrode 209.

Right ventricular cardiac signals sensed through use of defibrillation electrodes are far-field signals, also referred to as RV morphology or RV shock channel signals. More particularly, a right ventricular shock channel signal may be detected as a voltage developed between the RV-coil 214 and the SVC-coil 216. A right ventricular shock channel signal may also be detected as a voltage developed between the RV-coil 214 and the can electrode 209. In another configuration the can electrode 209 and the SVC-coil electrode 216 may be electrically shorted and a RV shock channel signal may be detected as the voltage developed between the RV-coil 214 and the can electrode 209/SVC-coil 216 combination.

Left atrial cardiac signals may be sensed through the use of one or more left atrial electrodes 215, 218, which may be configured as epicardial electrodes. A left atrial sensing circuit 335 serves to detect and amplify electrical signals from the left atrium of the heart. Bipolar sensing and/or pacing in the left atrium may be implemented, for example, using the LA distal electrode 218 and the LA proximal electrode 215. Unipolar sensing and/or pacing of the left atrium may be accomplished, for example, using the vector from the LA distal electrode 218 to can electrode 209 or the LA proximal electrode 215 to can electrode 209.

A left ventricular sensing circuit 336 serves to detect and amplify electrical signals from the left ventricle of the heart. Bipolar sensing in the left ventricle may be implemented, for example, by sensing voltages developed between the LV distal electrode 213 and the LV proximal electrode 217. Unipolar sensing may be implemented, for example, by sensing voltages developed between the LV distal electrode 213 or the LV proximal electrode 217 to the can electrode 209.

Optionally, an LV coil electrode (not shown) may be inserted into the patient's cardiac vasculature, e.g., the coronary sinus, adjacent the left heart. Signals detected using combinations of the LV electrodes, 213, 217, LV coil electrode (not shown), and/or can electrodes 209 may be sensed and amplified by the left ventricular sensing circuitry 336. The output of the left ventricular sensing circuit 236 is coupled to the control system 320.

The outputs of the switching matrix 310 may be operated to couple selected combinations of electrodes 211, 212, 213, 214, 216, 217, 218, 254, and 256 to an evoked response sensing circuit 337. The evoked response sensing circuit 337 serves to sense and amplify voltages developed using various combinations of electrodes for cardiac response classification in accordance with embodiments of the invention.

In the embodiments described below, various combinations of pacing and sensing electrodes may be utilized in connection with pacing and sensing the cardiac signal following the pace pulse to classify the cardiac response to the pacing pulse. For example, in some embodiments, a first electrode combination is used for pacing a heart chamber and a second electrode combination is used to sense the cardiac signal following pacing. In other embodiments, the same electrode combination is used for pacing and sensing.

The pacemaker control circuit 322, in combination with pacing circuitry for the left atrium, right atrium, left ventricle, and right ventricle may be implemented to selectively generate and deliver pacing pulses to the heart using various electrode combinations. The pacing electrode combinations may be used to effect bipolar or unipolar pacing of the heart chambers as described above.

As described above, bipolar or unipolar pacing pulses may be delivered to a heart chamber using one of the pacing vectors as described above. The electrical signal following the delivery of the pacing pulses may be sensed through various sensing vectors coupled through the switch matrix 310 to the cardiac response classification processor 325 and used to classify the cardiac response to pacing.

The switching matrix 310 may be arranged to provide connections to various configurations of pacing and defibrillation electrodes. The outputs of the switching matrix 310 may be coupled to an evoked response (ER) sensing circuit 337 that serves to sense and amplify cardiac signals detected between the selected combinations of electrodes. The detected signals are coupled through the ER amplifier 337 to a cardiac response classification processor 325. The cardiac response classification processor 325 includes circuitry configured to determine the cardiac response to a pacing stimulation. The presence or absence of an evoked response may be determined based on the amplitude, peak value, peak timing, and/or other morphological features of the cardiac signal sensed following the pacing pulse in accordance with embodiments of the invention.

In one implementation, the cardiac pacemaker/defibrillator 300 may utilize the evoked response channel 337 to sense for the atrial evoked response (AER) as described herein. The cardiac pacemaker/defibrillator 300 may utilize the right atrial sensing channel 331 to sense for retrograde P-waves in the right atrium. The cardiac pacemaker/defibrillator 300 may utilize the left atrial sensing channel 335 to sense for retrograde P-waves in the left atrium.

A patient internal medical device (PIMD) of the present invention may be used within the structure of an advanced patient management (APM) system. The APM allows physicians to remotely and automatically monitor cardiac and respiratory functions, as well as other patient conditions. In one example, a PIMD implemented as a cardiac pacemaker, defibrillator, or resynchronization device may be equipped with various telecommunications and information technologies that enable data collection, diagnosis, and treatment of the patient. Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

A number of the examples presented herein involve block diagrams illustrating functional blocks used for coordinated monitoring, diagnosis and/or therapy functions in accordance with embodiments of the present invention. It will be understood by those skilled in the art that there exist many possible configurations in which these functional blocks can be arranged and implemented. The examples depicted herein provide examples of possible functional arrangements used to implement the approaches of the invention.

It is understood that the components and functionality depicted in the figures and described herein can be implemented in hardware, software, or a combination of hardware and software. It is further understood that the components and functionality depicted as separate or discrete blocks/elements in the figures in general can be implemented in combination with other components and functionality, and that the depiction of such components and functionality in individual or integral form is for purposes of clarity of explanation, and not of limitation.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of detecting sub-threshold atrial pacing, comprising:
   performing an atrial capture threshold test;
   generating a retrograde P-wave template in response to atrial non-capture identified during the atrial capture threshold test;
   delivering a pacing pulse to an atrium during a cardiac cycle;
   identifying a retrograde P-wave during the cardiac cycle using the generated retrograde P-wave template, the retrograde P-wave indicative of sub-threshold atrial pacing; and
   adjusting delivery of the pacing pulse to the atrium in a subsequent cardiac cycle in response to identifying the retrograde P-wave.

2. The method of claim 1, wherein adjusting delivery of the pacing pulse comprises initiating an atrial capture threshold test.

3. The method of claim 1, wherein adjusting delivery of the pacing pulse comprises re-evaluating one or both of the pacing pulse amplitude and pulse width.

4. The method of claim 1, wherein identifying the retrograde P-wave comprises determining one or more of the frequency content, amplitude, slew rate, and timing of an atrial response.

5. The method of claim 1, comprising confirming presence of the retrograde P-wave prior to adjusting delivery of the pacing pulse.

6. The method of claim 1, wherein adjusting delivery of the pacing pulse comprises temporarily increasing one or both of the pacing pulse amplitude and pulse width.

7. The method of claim 1, wherein identifying the retrograde P-wave comprises sensing an atrial response during a post ventricular atrial refractory period.

8. The method of claim 1, wherein identifying the retrograde P-wave comprises sensing an atrial response within a range of about 50 milliseconds and about 300 milliseconds after a ventricular pace.

9. The method of claim 1, wherein adjusting delivery of the pacing pulse comprises altering the timing of a scheduled atrial capture threshold test.

10. A cardiac system, comprising:
    a plurality of implantable electrodes configured for one or both of sensing a cardiac signal and delivering cardiac pacing pulses to a patient;
    a housing configured for implantation in the patient;
    memory; and
    a controller provided in the housing and coupled to the plurality of implantable electrodes, the controller configured to execute program instructions stored in the memory, wherein controller execution of the stored program instructions cause the cardiac system to perform an atrial capture threshold test, generate a retrograde P-wave template in response to atrial non-capture identified during the atrial capture threshold test, deliver a pacing pulse to an atrium of the patient's heart during a cardiac cycle, identify a retrograde P-wave indicative of sub-threshold atrial pacing during the cardiac cycle using the generated retrograde P-wave template, and adjust delivery of the pacing pulse to the atrium in a subsequent cardiac cycle in response to identifying the retrograde P-wave.

11. The cardiac system of claim 10, wherein the controller is configured to initiate an atrial capture threshold test in response to identifying the retrograde P-wave.

12. The cardiac system of claim 10, wherein the controller is configured to re-evaluate one or both of the pacing pulse amplitude and pulse width in response to identifying the retrograde P-wave.

13. The cardiac system of claim 10, wherein the controller is configured to determine one or more of the frequency content, amplitude, slew rate, and timing of an atrial response in order to identify the retrograde P-wave.

14. The cardiac system of claim 10, wherein the controller is configured to confirm presence of the retrograde P-wave prior to adjusting delivery of the pacing pulse.

15. The cardiac system of claim 10, wherein the controller is configured to temporarily increase one or both of the pacing pulse amplitude and pulse width in response to identifying the retrograde P-wave.

16. The cardiac system of claim 10, wherein the controller is configured to sense for the retrograde P-wave during a post ventricular atrial refractory period.

17. A cardiac system, comprising:
 means for performing an atrial capture threshold test;
 means for generating a retrograde P-wave template in response to atrial non-capture identified during the atrial capture threshold test;
 means for delivering a pacing pulse to an atrium during a cardiac cycle;
 means for identifying a retrograde P-wave during the cardiac cycle using the generated retrograde P-wave template to identify the retrograde P-wave, the retrograde P-wave indicative of sub-threshold atrial pacing; and
 means for adjusting delivery of the pacing pulse to the atrium in a subsequent cardiac cycle in response to identifying the retrograde P-wave.

* * * * *